(12) United States Patent
Li et al.

(10) Patent No.: US 10,905,703 B2
(45) Date of Patent: Feb. 2, 2021

(54) PREPARATION OF A COMPOSITION CONTAINING STILBENE GLYCOSIDE

(71) Applicant: Shiming Li, Glastonbury, CT (US)

(72) Inventors: Shiming Li, Glastonbury, CT (US); Jianfeng Zhan, Hubei (CN)

(73) Assignee: Huanggang Normal University, Hubei (CN)

( * ) Notice: Subject to any disclaimer, the term of this patent is extended or adjusted under 35 U.S.C. 154(b) by 0 days.

(21) Appl. No.: 16/297,672

(22) Filed: Mar. 10, 2019

(65) Prior Publication Data

US 2019/0201428 A1 Jul. 4, 2019

Related U.S. Application Data

(63) Continuation-in-part of application No. 14/960,337, filed on Dec. 4, 2015, now Pat. No. 10,272,127.

(51) Int. Cl.
| | |
|---|---|
| *A61K 36/704* | (2006.01) |
| *A61K 31/7034* | (2006.01) |
| *A61K 36/70* | (2006.01) |
| *A61P 3/10* | (2006.01) |
| *C07H 15/203* | (2006.01) |

(52) U.S. Cl.
CPC .......... *A61K 31/7034* (2013.01); *A61K 36/70* (2013.01); *A61K 36/704* (2013.01); *A61P 3/10* (2018.01); *C07H 15/203* (2013.01); *A61K 2236/15* (2013.01); *A61K 2236/333* (2013.01); *A61K 2236/39* (2013.01); *A61K 2236/51* (2013.01); *C07B 2200/09* (2013.01)

(58) Field of Classification Search
None
See application file for complete search history.

(56) References Cited

U.S. PATENT DOCUMENTS

| 10,272,127 B2 * | 4/2019 | Li ................... A61K 31/7034 |
| 2004/0052879 A1 * | 3/2004 | Ravagnan .......... A61K 2300/00 |
| | | 424/762 |
| 2015/0005533 A1 * | 1/2015 | Boue ....................... G21K 5/00 |
| | | 568/729 |
| 2016/0008386 A1 * | 1/2016 | Wu ..................... A61K 31/7034 |
| | | 514/25 |

FOREIGN PATENT DOCUMENTS

| CN | 1957991 | * | 5/2007 |
| CN | 101787060 | * | 7/2010 |
| CN | 102060889 | * | 5/2011 |
| CN | 102731586 | * | 10/2012 |

OTHER PUBLICATIONS

Ling, S. et al. Biological Activities of 2,3,5,4'-Tetrahydroxystilbene-2-O-beta-D-Glucoside in Antiaging and Antiaging Related Disease Treatments. Oxidative Medicine and Cellular Longevity vol. 2016. (Year: 2016).*
Lv, L. et al. Antioxidant Activity of Stilbene Glycoside from PM Thunb In vivo. Food Chemistry 104(4)1678-1681, 2007. (Year: 2007).*
Wu X. et al. Toxicity of Raw and Processed Roots of PM. Fitoterapia 83:469-475, 2012. (Year: 2012).*
Li C. et al. Screening for Main Components Associated with the Idiosyncratic Hepatotoxicity of a Tonic Herb, PM. Frontiers of Medicine 11(2)253-265, 2017. (Year: 2017).*
Tang, W. Hypoglycemic Effects of Stilbene Glycoside from PM in Type 2 Diabetes and its Mechanism of Action. Dissertation at Rutgers Oct. 2015 (Year: 2015).*

* cited by examiner

Primary Examiner — Ralph J Gitomer
(74) Attorney, Agent, or Firm — Bin Lu

(57) ABSTRACT

Disclosed is a method of processing *Polygonum multiflorum*, the method contains preparing a root extract solution and placing the solution under UV light for 1 to 24 hours. Also disclosed is a composition prepared from the method that can be for use in the prevention, treatment, and management of diabetes in human and animal subjects.

8 Claims, 13 Drawing Sheets

Effect of PM extract on selected markers from insulin signaling pathway

FIG. 6
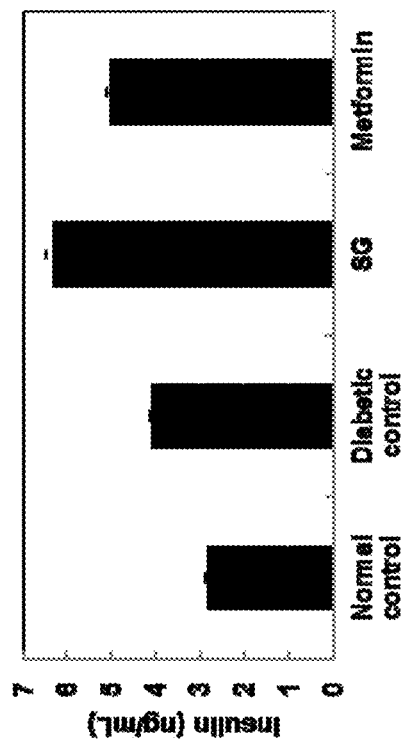
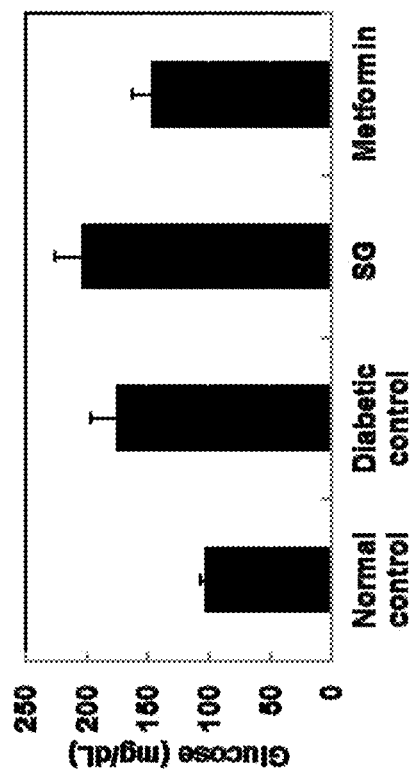
Effect of SG on serum glucose and insulin levels.

Effect of SG on (A) glucose tolerance and (B) insulin tolerance

Chemical structures of (A) *trans*-SG and (B) *cis*-SG.

NMR and LC-MS spectrums of *trans*-SG and *cis*-SG

PREPARATION OF A COMPOSITION CONTAINING STILBENE GLYCOSIDE

CROSS-REFERENCING

This application claims the benefit of application Ser. No. 14/960,337, filed on Dec. 4, 2015, which is hereby incorporated in reference by its entireties for all purposes.

FIELD OF THE INVENTION

The invention relates to a composition for use in the prevention, treatment, and management of diabetes in human and animal subjects. More specifically, the present invention provides a composition extracted from one or more plants of *Fallopia* genera, and methods of using and preparing the composition thereof.

BACKGROUND OF THE INVENTION

Diabetes is a one of the leading causes of death in the U.S. and the number and percentage of U.S. population with diabetes is rapidly increasing. Today, 25.8 million children and adults—8.3% of the U.S. population—have diabetes. The number will reach 366 million by 2030, according to the World Health Organization. the total medical costs annually in the U.S. for diabetes exceeded $100 billion.

There are mainly three types of diabetes: type 1, type 2, and gestational diabetes. Among them, type 2 diabetes, also referred to as non-insulin dependent diabetes mellitus (NIDDM), represents more than 90% of all diabetes patients. Insulinis a hormone that regulates the body metabolism mainly by promoting the absorption of glucose from the blood to muscles and other tissues. Type 2 diabetes is characterized with insulin resistance, which is a diminished ability of insulin to exert its biologic action on regulating glucose. Insulin resistance, related strongly to a sedentary lifestyle, is also associated with a variety of abnormalities including obesity, hypertension, hyperlipidemia, and hyperuricemia. Thus, there is a clear need to develop diabetes therapies.

However, current therapeutic strategies for diabetes, especially type 2 diabetes are limited and major anti-diabetic agents generally suffer from inadequate efficacy and high side effects. Side effects from diabetes drugs are often severe, which include hypoglycemia, lactic acidosis, idiosyncratic liver cell injury, permanent neurological deficit, digestive discomfort, headache, dizziness, and even death. For instance, pioglitazone, rosiglitazone, two widely used diabetes drugs, are found to promote weight gain, a major adverse event associated with these two drugs' effects on adipose cell differentiation and triglyceride storage.

There is an urgent and strong need to develop an effective therapy with few adverse effects for diabetes patients.

SUMMARY OF THE INVENTION

This invention provides a composition extracted from *Fallopia* genera plants. As a naturally derived agent, the composition provides a wider range of utilities for preventing, treating and managing diabetes safely and effectively.

One aspect of this invention relates to a composition for use in the prevention, treatment, and management of diabetes in human and animal subjects, comprising 2,3,5,4-tetrahydroxystilbene 2-O-β-glucopyranoside (stilbene glycoside) collected from one or more plants selected from the group consisting of *Fallopia* genera of plants.

The stilbene glycoside can be cis-stilbene glycoside and/or trans-stilbene glycoside. More specifically, the stilbene glycoside contains 0-99 wt % cis-stilbene glycoside and 100-1 wt % trans-stilbene glycoside.

Typically, the cis-stilbene glycoside described above is derived from the trans-stilbene glycoside by exposing to UV light.

One example of the *Fallopia* genera plants is *Polygonum multiflorum* (PM).

The diabetes treated can be type 2 diabetes.

Another aspect of this invention relates to a method for processing PM. The method is carried out as follows: (i) crushing dried roots of PM to powder; (ii) extracting the PM powder with an ethanol solution under the room temperature for at least 2 days to obtain an ethanolic extract, the ratio of solution to solid being about 1:10 (v/w); (iii) evaporating and concentrating the ethanolic extract under reduced pressure to obtain a dried extract; (iv) subjecting the dried extract to macroporous resin chromatography, followed by eluting the resin with ethanol solutions of different concentrations to obtain a first eluant; (v) evaporating and drying the first eluant under reduced pressure to obtain PM extract powder; (vi) dissolving the obtained PM extract powder in an aqueous solution to obtain a PM solution; and (vii) placing the PM solution under UV light for 1 to 24 hours. An UV-treated PM solution is finally obtained.

The PM solution discussed above can contain trans-stilbene glycoside at a concentration of 1-50 mg/ml. Preferably, the PM solution contains trans-stilbene glycoside at a concentration of 2-20 mg/ml.

Advantageously, the UV light used has a wavelength of approximately 365 nm.

The PM solution can be placed under the UV light for 5-15 hours. Also, it can be placed under the UV light for 5-10 hours.

Further, the UV-treated PM solution contains cis-stilbene glycoside and trans-stilbene glycoside and the ratio of cis-stilbene glycoside to trans-stilbene glycoside is greater than 1:1. One example of the ratio of cis-stilbene glycoside to trans-stilbene glycoside is between 3:1 and 5:1. Another example of the ratio is at or greater than 10:1.

Moreover, the UV-treated PM solution can be treated by HPLC to obtain a second eluant followed by evaporating and drying under reduced pressure to obtain UV-treated PM extract powder.

The first eluant and the PM extract powder obtained thereafter each comprise trans-stilbene glycoside. On the other hand, the second eluant and the UV-treated PM extract powder obtained thereafter each comprise cis-stilbene glycoside.

The HPLC described in step (vii) above is performed under the conditions that include a HYPERSIL-C18 column, a mobile phase gradient of 15 min from 40% acetonitrile to 65% acetonitrile, and a flow rate of 8 mL/min.

Still another aspect of this invention relates to a composition prepared from the above method of processing PM. Consequently, the composition contains cis-stilbene glycoside and trans-stilbene glycoside and the ratio of cis-stilbene glycoside to trans-stilbene glycoside is greater than 1:1. As enumerated above, one example of the ratio of cis-stilbene glycoside to trans-stilbene glycoside is between 3:1 and 5:1 and another example of the ratio is at or greater than 10:1.

Yet another aspect of this invention relates to a method of extracting cis-stilbene glycoside from one or more plants selected from the group consisting of *Fallopia* genera of plants. The method has the steps of: (i) providing dried roots from one or more plants selected from the group consisting of *Fallopia* genera of plants; (ii) preparing an UV-treated root extract solution using the above method of processing PM; and (iii) purifying cis-stilbene glycoside from the UV-treated root extract solution, wherein the purification comprises high performance chromatography or recrystallization.

The cis-stilbene glycoside prepared from the just-described method can be in a composition for prevention, treatment, and management of diabetes in human and animal subjects.

Still another aspect of this invention relates to a method for treatment and management of diabetes. The method includes administering an effective dose of a composition to a subject in need thereof and the composition is prepared from the above method of processing PM.

Examples of the composition are enumerated above, which include cis-stilbene glycoside and/or trans-stilbene glycoside.

Yet another aspect of this invention relates to a method converting trans-stilbene glycoside to cis-stilbene glycoside at a conversion rate of at least 50%. The method includes the steps of (i) providing a solution comprising trans-stilbene glycoside at a concentration of 1-50 mg/ml; and (ii) placing the solution under UV light having a wavelength of approximately 365 nm for 1 to 24 hours.

The details of the invention are set forth in the drawing and description below. Other features, objects, and advantages of the invention will be apparent from the description and from the claims.

BRIEF DESCRIPTION OF THE DRAWINGS

These drawings illustrate certain aspects of some of the embodiments of the present invention, and should not be used to limit or define the invention.

FIG. 6 is a diagram that shows effect of stilbene glycoside on serum glucose and insulin levels.

DETAILED DESCRIPTION

*Polygonum multiflorum* (PM), other names He Shou Wu or Fo-ti, is one of the *Fallopia* genera plants. It is used in China as a longevity tonic for graying hair, premature aging, weakness and other dysfunctions. The root of PM is used as a tonic and an anti-aging agent in many remedies in traditional Chinese medicine.

The medicinal effects of PM in the treatment of these age-related diseases are possibly mediated by the antioxidant capacity of this plant. In 2005 the extracts of 30 Chinese medicinal plants were studied systematically for their antioxidant activities and PM root was found to be among the highest for both aqueous and methanol extracts. PM extract has been found both in vitro and in vivo to possess antioxidant activity. Research indicates that PM enhances the cellular antioxidant activity, increases the function of superoxide dismutase (SOD), significantly inhibits the formation of oxidized lipids, represses lipid peroxidation in rat heart mitochondria and enhances antioxidant enzymes in the liver.

By analysis technologies such as TLC, HPLC, and LC-MS, many components in PM extracts have been identified, which include 2,3,5,4-tetrahydroxystilbene-2-O-β-D-glucoside, emodin-8-O-β-D-glucoside, physcion-8-O-β-D-glucoside, emodin, chrysophanol, rhaponticoside, torachrysone-8-O-β-D-glucoside, chrysophanol-8-O-β-D-glucoside, physcion and so on.

Figure 1:
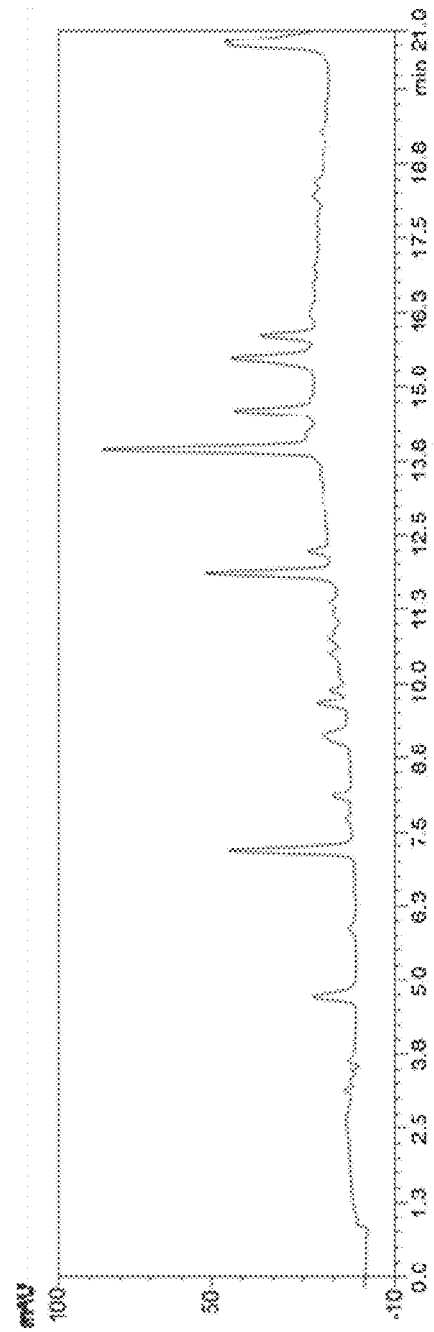
FIG. 1 is a diagram illustrating a HPLC chromatogram for the PM extract.
Figure 2:
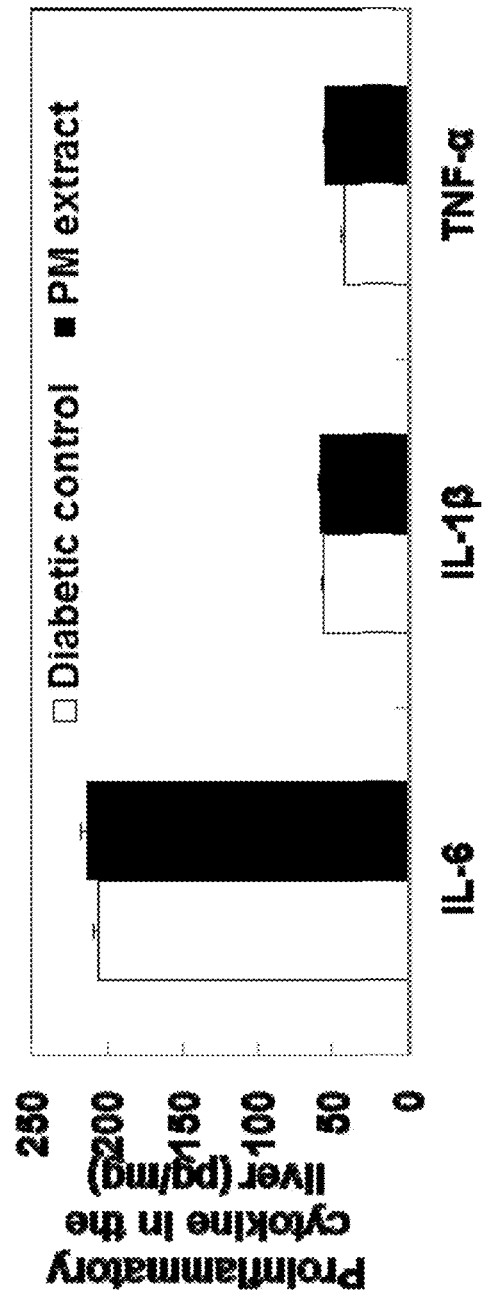
FIG. 2 is a bar diagram that shows effect of the PM extract on levels of IL-6, IL-1b, and TNF-a in liver samples.

2,3,5,4-tetrahydroxystilbene 2-O-β-glucopyranoside (stilbene glycoside) with the chemical structure $C_{20}H_{22}O_9$ and molecular weight 406.39, is a white amorphous powder, soluble in water, methanol and ethanol. It is stable in water solutions, but high temperature (>80° C.) might affect its stability; it's very unstable in acid. stilbene glycoside is the major active compound in PM, and the concentration in the roots of PM can reach 3%-6%. According to Chinese Food and Drug Administration, stilbene glycoside is used as an index of quality control for PM products and the concentration of stilbene glycoside in commercial PM products has to be higher than 1%.

stilbene glycoside is a type of stilbene derivative, and other well-known stilbene compounds in stilbene family include resveratrol (FIG. 2.1 B) and pterostilbene. The only difference between structures of stilbene glycoside and resveratrol is the glycoside portion. Because of the additional hydroxyl group at the iso-position, stilbene glycoside has higher antioxidant activity than resveratrol.

Using Ultra-performance liquid chromatography—time-of-flight mass spectrometry (UPLC-Q-TOF/MS) and HPLC-UV, the pharmacokinetics, bioavailability, absorption, and metabolism of stilbene glycoside were studied in rats following a single intravenous or oral administration. It was found that stilbene glycoside was rapidly distributed (within 30 min) and then eliminated from rat plasma. Absolute bioavailability of stilbene glycoside was 40%. Total recovery of unchanged stilbene glycoside within 24 hr were low (0.041% in bile, 0.06% in feces), whereas the amount of unchanged stilbene glycoside excreted in the urine within 24 hr was lower than Lower Limit of Quantification (LLOQ). stilbene glycoside was excreted mainly in the forms of metabolites, including monoglucuronide and the deglycosidated form which is more stable.

Cis-stilbene polyphenols are found to always have higher activities than their trans-isomers. Cis-stilbene glycoside was first discovered in PM roots in 2002 and the structure was identified with NMR. The level of cis-stilbene glycoside was found to be very low in PM, making it very hard to isolate and enrich. To this date there is rarely any endeavor which enriches the level of cis-stilbene glycoside in PM and studies its activity. Yet, cis-stilbene polyphenols could be induced with isomerization from trans-stilbenes with UV-light. Cis-stilbene glycoside is an efficacious compound in PM responsible for its anti-diabetic activities.

EXAMPLES

Example 1: Anti-Diabetic Effect of a PM Extract

Preparation of Extract from PM Roots

Dried root powder of PM was purchased from Anguo Mayway Herb Company Ltd., An Guo, Heibei Province, China, and followed extraction procedure of Lishuang Lv with slight modification. Briefly, the dried roots of PM were crushed and extracted with 60% ethanol, at a ratio of solution to solid of 1:10 (v/w), at room temperature for 2 days. The plant material was filtered off, and the ethanolic extracts were combined and concentrated under reduced pressure using a rotary evaporator. The dry extract obtained was then subjected to open column chromatography (CC) packed with macroporous resin. The column was eluted stepwise with each of 9 different concentrations of ethanol (10%, 20%, 30%, 40%, 50%, 60%, 70%, 80% and 90%). The 40% aqueous-ethanol fraction was then concentrated under reduced pressure using a rotary evaporator. The powder obtained was subjected to HPLC for analysis, and used for animal study later.

HPLC Analysis of a PM Extract

PM extract was analyzed by a Waters Acquity HPLC system coupled with a UV detector (Waters, Milford, Mass.). A 250 mm×4.6 mm inner diameter, 5 µm, HYPERSIL-C18 column was used. For binary gradient elution, mobile phases A (100% water with 0.2% formic acid) and B (acetonitrile) were used. The flow rate was maintained at 1 mL/min, and the mobile phase began with 8% B. It was followed by progressive linear increases in B to 35% at 17 min, to 90% at 18 min, and maintained at 90% until 21 min. The injection volume was 10 µL for each sample.

KK CgAy/J Yype 2 Diabetic Mouse Model

Transgenic female KK CgAy/J diabetic mice were purchased from Jackson labs (Barr Harbor, Me.) and were housed in stainless steel wire-bottomed cages and acclimatized under laboratory conditions (19-23° C., humidity 60%, 12 h light/dark cycle). The mice were divided into two groups with 10 each, and fed with Western HFD (Research Diets, New Brunswick, N.J.) composed of 20 kcal % protein, 20 kcal % carbohydrate, and 60 kcal % fat (from butter). Group I: Diabetic control which had free access to drinking water; Group II: Treatment group which had free access to drinking water with 0.075% of PM extract. Body weight, food and water uptake of the mice were taken on a regular basis. After 7 weeks, all the experimental mice were sacrificed. Body weight, blood glucose level and lipid profile were recorded. Blood glucose was measured with blood glucose test strips from Contour, and lipid profile was measured with PTS Panels test strips. The weight of parametrial fat, retro-peritoneal fat and brown fat was recorded. Liver, spleen and kidney were removed and weighed as well.

Biochemical Assays

Blood sample was collected and centrifuged at 12,500 rpm for an hour. Serum insulin level was measured with a commercial kit (Cayman Chemical, Detroit, Mich.), and performed according to the protocol. Liver and fat tissues were homogenized, lysed with lysis buffer [(0.5% (w/v) sodium lauryl sarkosinate+10 mM EDTA+0.5 mg/ml proteinase K+0.1 mg/ml RNase A in 50 mM Tris-Base, pH 8.0)], centrifuged and protein of homogenates quantified using a BCA protein assay kit (Pierce Chemical, Rockford, Ill.).

ELISA Assay

The levels of Pro-inflammatory cytokines (IL-1$\beta$, IL-6 and TNF-$\alpha$) in the liver homogenates of control and experimental groups of KK CgAy/J mice were determined by specific ELISA kits according to the manufacturer's instructions (Camarillo, Calif.). The capture antibody, diluted with PBS, was used to coat a 96-well plate overnight at room temperature. The plate was then washed, blocked (1% BSA, 5% sucrose in PBS with 0.05% $NaN_3$), and washed again. The standards were added to the plate leaving at least one zero concentration well and one blank well. The diluted samples (1:5-1:20) were then added to the plate. After incubating for 2 h, the plates were washed and the detection antibody was added. After incubating for another 2 h the plates were washed and Streptavidin-HRP was added. After 20 min incubation, the plates were washed, and substrate ($H_2O_2$) and tetramethylbenzidine were added. After another 20 min incubation, the stop solution (2 N of $H_2SO_4$) was added and then, plates were read with a microplate reader at a wavelength of 450 nm. Standard plots were constructed by using standard cytokines and the concentrations for unknown samples were calculated from the standard plot.

Western Blotting

The sample of liver or fat homogenates (60 µg of protein) in 4× loading buffer was denatured at 95° C. for 5 min, and subjected to SDS-polyacrylamide gel (4-10%) electrophoresis. The gel then was transferred onto a polyvinylidene difluoride membrane (Bio Rad, Hercules, Calif.), and the membrane was blocked with TBS-T (20 mM Tris-HCl, 150 mM NaCl, and 0.1% Tween 20, pH 7.4), containing 5-7% nonfat dried milk. The blocked membrane was incubated at 4° C. overnight with 1:500 dilution of monoclonal antibody for IR-$\alpha$, IRS-1 (liver) and Glut4 (fat) (Santa Cruz Biotechnology, Santa Cruz, Calif.). The immunoblotted membrane was incubated at room temperature for 2 hr with secondary anti-rabbit or anti-mouse IgG antibodies conjugated with horseradish peroxidase and then exposed on X-ray film with ECL detection reagent (Amersham Pharmacia Biotech, Piscataway, N.J.). Bands were quantified using the Adobe Photoshop program with scanning process.

All experiments and analyses were performed at least in triplicate. Results are expressed as means±SE. Statistical analyses were performed using the Student's T-test. * denotes the difference was statistically significant ($p<0.05$).

Results (1) Hypoglycemic Effect of PM in KK CgAy/J Diabetic Mice

Results are shown in Table 1 below. After 7 weeks of PM extract administration in drinking, body weight of transgenic KK Cg/Ay mice was comparable between control group and treatment group after 7 weeks test period. Triglyceride level was significantly higher in the treatment group, but the other lipid parameters, such as HDL, LDL and total cholesterol almost stayed the same in the two groups. Weight of liver and kidney also showed no difference in the two groups, but spleen showed a significant weight loss. At the same time, the hyperglycemia of transgenic diabetic KK Cg/Ay mice was almost completely reverted to normal by the PM extract treatment, since the glucose level in the control group and treatment group is 233.6 mg/dl and 121.6 mg/dl, respectively. That indicates that the PM extract had a strong hypoglycemic effect.

TABLE 1

Anti-diabetic effects of feeding PM extract in the drinking water to female KK CgAy/J mice

| List of Assays | Group 1 | Group 2 |
| --- | --- | --- |
| Body weight (g) | 40.46 ± 1.91 | 41.06 ± 0.75 |
| Glucose (mg/dl) | 233.56 ± 33.18 | 121.60 ± 13.07** |
| Triglyceride (mg/dl) | 238.44 ± 13.80 | 271.70 ± 34.59 |
| Total cholesterol (mg/dl) | 173.33 ± 3.38 | 179.30 ± 4.53 |
| HDL (mg/dl) | 90.00 ± 2.38 | 86.00 ± 3.07 |
| LDL (mg/dl) | 35.62 ± 5.77 | 39.00 ± 5.96 |
| Parametrial fat (g) | 4.73 ± 0.34 | 4.96 ± 0.31 |
| Retroperitoneal fat (g) | 0.58 ± 0.06 | 0.75 ± 0.04* |
| Brown fat (g) | 0.80 ± 0.07 | 0.78 ± 0.06 |
| Liver (g) | 2.1 ± 0.17 | 2.09 ± 0.11 |
| Spleen (g) | 0.15 ± 0.01 | 0.12 ± 0.01* |
| Kidney (g) | 0.34 ± 0.02 | 0.37 ± 0.01 |

**$P < 0.003$,
*$P < 0.05$ as determined by the Student' T-test.
Group 1 (drinking water);
Group 2 (0.075% PM extract in drinking water) for 7 weeks.

(2) Pro-Inflammatory Cytokine Levels in the Liver

Pro-inflammatory cytokine (IL-6, IL-1β, and TNF-α) levels in the liver were measured with commercial Elisa kits after seven weeks of PM treatment. From FIG. 2, levels of IL-6 and IL-1b didn't differ significantly between diabetic control group and PM group. However, for TNF-α the level slightly increased in PM treated group ($p<0.05$). The level of IL-6 was the highest among all three cytokines, at around 200 pg/mg.

(3) Markers for Insulin Signaling Pathway

Figure 3:
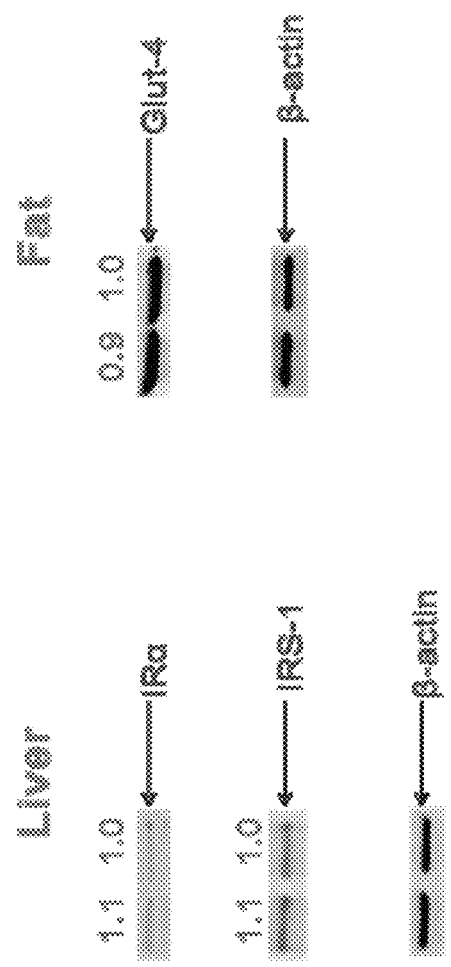
FIG. 3 is a diagram showing effect of the PM extract on selected markers from insulin signaling pathway.

The levels of selected marker from insulin signaling pathway including IR-α and IRS-1 from the liver and Glut4 from the fat, did not show any significant difference from diabetic control and PM group (see FIG. 3), which is consistent with our previous findings. Taken together, these results suggest that the hypoglycemic effect of PM extract was not mediated through insulin resistance.

(4) Serum Insulin Levels

Figure 4:
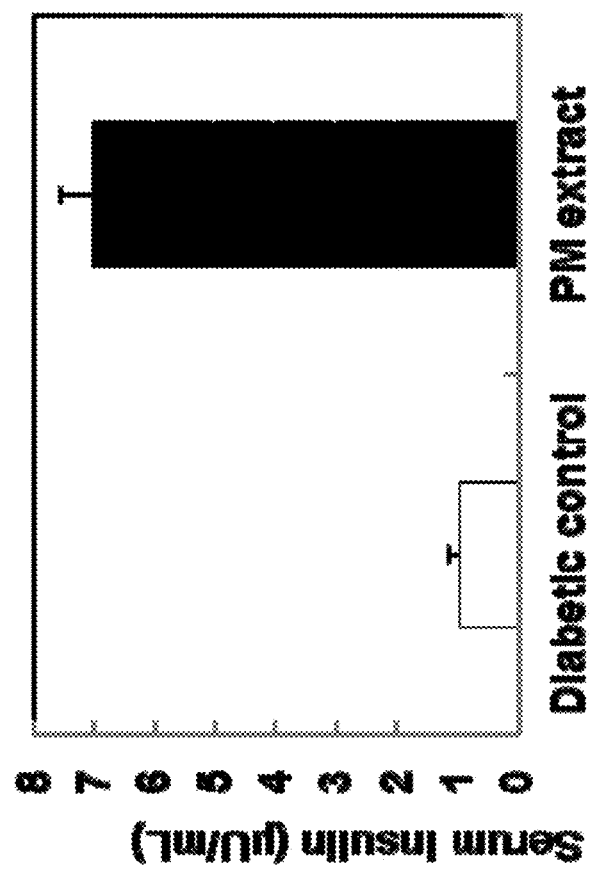
FIG. 4 is a diagram showing effect of the PM extract on serum insulin levels of KK CgAy/J mice.
Figure 5:
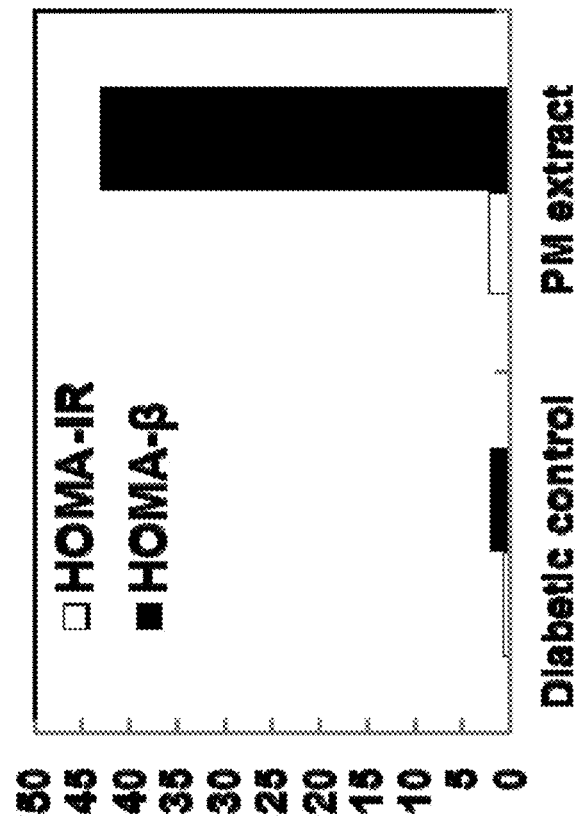
FIG. 5 is a diagram showing approximated insulin resistance (IR) and β cell function (β) from a HOMA model.

Serum insulin level significantly increased from 1 μU/ml in diabetic group to around 7 μU/ml in PM extract (FIG. 4), indicating that PM extract had a potent effect in stimulating insulin secretion.

(5) HOMA-β and HOMA-IR

Based on the calculation from Homeostatic Model Assessment (HOMA) model, HOMA-IR=Glucose*Insulin/405 and HOMA-β=(360*Insulin)/(Glucose-63); with fasting blood glucose and fasting blood insulin levels, insulin resistance increased slightly in PM group, but what's more significant is β cell function, which improved by nearly 20 fold from 2 to 45 after PM treatment.

Example 2: Evaluation of Stilbene Glycoside for its Anti-Diabetic Effect

Purification of Stilbene Glycoside

PM roots were extracted in the same manner as described in Example 1, and macroporous resin column was also used for separation. The column was eluted with 2 of 40% ethanol to get rid of impurities, and then with 1 of 50% ethanol. Fractions collected were monitored with HPLC analysis and the ones with pure stilbene glycoside were piled and concentrated under reduced pressure using a rotary evaporator. stilbene glycoside was analyzed with the same HPLC program as in 1.2.2.

Anti-Diabetic Effect of Stilbene Glycoside in Animal Study

Female KK CgAy/J mice were also utilized in this experiment and handled with the same protocol as in 1.2.3. The mice were divided into four groups with 10 each, and fed with Western HFD. Group I: Normal KK control mice which had free access to drinking water and normal chow; Group II: Diabetic control which had free access to drinking water and HFD; Group III: Treatment group which had free access to drinking water with 0.075% of PM-stilbene glycoside and HFD. Group IV: Positive control group which had free access to metformin at 300 mg/Kg and HFD. Body weight, food and water uptake of the mice were taken on a regular basis. After 12 weeks, all the experimental mice were sacrificed. Similar measurements were taken to the previous experiment with PM extract.

Before sacrifice, all the experimental mice were subjected to glucose and insulin tolerance tests. For glucose tolerance test, mice were fasted overnight and injected with glucose solution at 1 g/10 ml and 10 ml/kg body weight. The change in blood glucose level was monitored during the following two hours. For insulin tolerance test, mice were fasted for 5 hours and injected with insulin solution at 1 u/ml and 10 ml/kg body weight. The change in blood glucose level was monitored during the following two hours.

Results

At the end of the feeding experiment, mice were sacrificed and measured for blood glucose and blood insulin levels. Diabetic control KK CgAy/j mice had significantly higher level of blood glucose compared to normal KK mice, and it was effectively brought down by anti-diabetic drug metformin (300 mg/kg); however, diabetic mice treated with 0.075% stilbene glycoside in drinking water had elevated levels of serum glucose as well as serum insulin compared to diabetic control (see FIG. 6), suggesting it did not exert any hypoglycemic effect.

Figure 7:
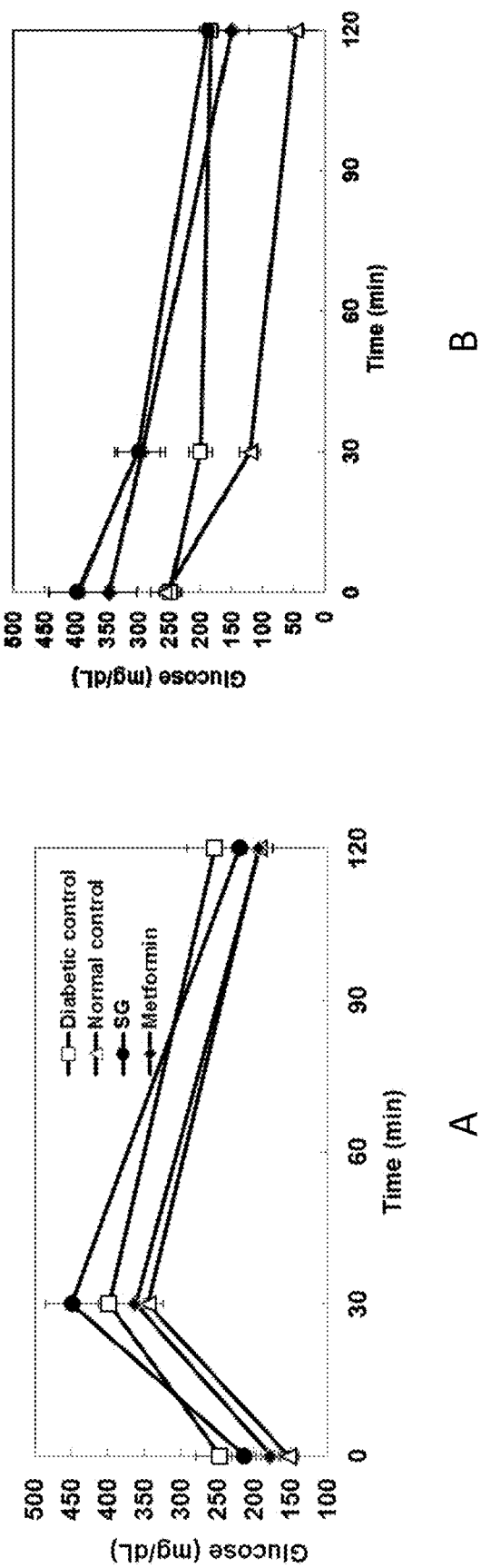
FIG. 7 is a diagram showing effect of stilbene glycoside on (A) glucose tolerance and (B) insulin tolerance.

To confirm the absence of hypoglycemic effect of stilbene glycoside, glucose tolerance test and insulin tolerance test were also carried out right before sacrifice. From the result of glucose tolerance test (FIG. 7A), 30 minutes after glucose injection (1 g/kg), the blood glucose levels in all experimental groups increased drastically, with stilbene glycoside group being the most elevated, and the blood glucose in stilbene glycoside group remained much higher than normal control and metformin groups at the end of the test, suggesting the diabetic mice in stilbene glycoside group were glucose intolerant. On the other hand, the insulin tolerance test displayed that both stilbene glycoside and metformin groups had higher level of glucose 30 minutes after insulin injection, however, two hours after injection, the blood glucose in metformin group dropped to a lower level than that of stilbene glycoside group (FIG. 7B). The positive control metformin had glucose tolerance and insulin tolerance similar to normal control, while the diabetic control had a high level of intolerance to both glucose and insulin, validating both models.

Example 3: Cis-Stilbene Glycoside as Possible Anti-Diabetic Agent from PM

It is imperative to develop a model which is convenient, stable, fast and inexpensive, and resembles human type 2 diabetes. The closer it came to sharing the metabolic characteristics of patients with type 2 diabetes, the more relevant and useful it would be in screening potential anti-diabetic agents. In the literature C57BL/6 (C57) mice are widely used in a diet induced model for type 2 diabetes. This strain becomes obese, hyperglycemic and insulin resistant when fed a HFD and it was concluded that the high-fat diet-fed C57 mouse model is a robust model for impaired glucose tolerance (IGT) and early type 2 diabetes, which may be used for studies on pathophysiology and development of new treatment. On the other hand, CF-1 mouse is an excellent model for obesity and it has been traditionally employed by our lab to study the anti-obesity effect of a variety of nutraceuticals. However, the suitability of HFD-induced CF-1 mouse as a model for type 2 diabetes was never explored in literature. Once the most appropriate model is identified, it would be used to test the anti-diabetic effects of pure trans- and cis-stilbene glycoside, and to confirm if the hypoglycemic effect of PM extract stems from cis-stilbene glycoside.

Purification of Cis-Stilbene Glycoside with Isomerization from Trans-Stilbene Glycoside Trans-stilbene glycoside was generated as described in preparation of a PM extract of Example 1. Pure trans-stilbene glycoside was dissolved in large volume of water and placed under UV-light over night. The reaction was monitored with HPLC analysis and the solution after UV exposure was concentrated, filtered, and subjected to preparative HPLC. A HYPERSIL-C18 column was used and mobile phase gradient of 40% to 65% B (acetonitrile) over 15 min was chosen. The flow rate was maintained at 8 mL/min. Pure cis-stilbene glycoside generated was piled, concentrated with a rotary evaporator and dried with a freeze drier.

Identification with Nuclear Magnetic Resonance Spectroscopy (NMR) and Liquid Chromatography-Mass Spectroscopy (LC-MS)

$^1H$ NMR and $^{13}C$ NMR spectra were acquired for both trans-stilbene glycoside and cis-stilbene glycoside on an AMX-500 spectrometer (Bruker, Rheinstetten, Germany) at Department of Chemistry, Rutgers University. For NMR analysis, all compounds were dissolved in $CD_3OD$.

LC-MS was performed for both isomers with a TIC detector. Prior to LC-MS analysis, all samples were filtered through a 0.45 μm PTFE syringe filter. ChemStation software (Version 3.01) was used for data acquisition and analysis. Ionization parameters included: capillary voltage, 3.5 kV; nebulizer pressure, 35 PSI; drying gas flow, 10.0 mL/min; and drying gas temperature, 350° C. MSD signal parameters included: mode, Selected Ion Monitoring (SIM); fragmentor voltage, 70V; gain, 1.0; dwell time, 144 msec; and % relative dwell time, 25.

Animal Study with Trans- and Cis-Stilbene Glycoside Extracts

Female KK mice were purchased from Jackson labs (Barr Harbor, Me.) and were housed in stainless steel wire-bottomed cages and acclimatized under laboratory conditions (19-23° C., humidity 60%, 12 h light/dark cycle). Normal control mice (n=10) were fed with control diet which was normal Chow 5001 from LabDiet (St. Louis, Mo.) and was composed of 28.5 kcal % protein, 58 kcal % carbohydrate and 13.5 kcal % fat. Diabetic control mice (n=10) were induced with HFD (Research Diets, New Brunswick, N.J.) composed of 20 kcal % protein, 20 kcal % carbohydrate, and 60 kcal % fat (from butter) for 18 weeks. Three solutions were administered to mice (n=10 each) on HFD ad libitum and the compositions are shown below. Solution 1: pure trans-stilbene glycoside (0.05% in drinking water), HPLC chromatogram in FIG. 3.2 (A); Solution 2: 60% ethanol extract of PM root powders, obtained according to procedure in Section 1.2.1 (proportion of cis-stilbene glycoside to trans-stilbene glycoside is approximately 1:20, 0.075% in drinking water), HPLC chromatogram in FIG. 3.2 (B); Solutions 3: obtained from exposing solution 2 under UV-light overnight (proportion of cis-stilbene glycoside to trans-stilbene glycoside is approximately 2:3, 0.075% in drinking water), HPLC chromatogram in FIG. 3.2 (C). After 18 weeks, body weight and blood glucose of all mice were measured.

Screening of Mice Model for Type 2 Diabetes

CF-1 mice and C57BL/6 (C57) mice (male and female) were purchased from Charles River laboratories (Horsham, Pa.) and were housed in stainless steel wire-bottomed cages and acclimatized under laboratory conditions (19-23° C., humidity 60%, 12 h light/dark cycle). Each strain was divided into four groups with ten mice each: M-control, male mice on normal diet; M-HF, male mice on Western HFD; F-control, female mice on normal diet; F-HF, female mice on Western HFD. All the mice had access to drinking water ad libitum. Body weight and nonfasting glucose levels were taken at week 5, 8 and 12. At the end of week 12, all the experimental mice were sacrificed. Lipid profile was measured with PTS Panels test strips; parametrial fat, retroperitoneal fat and brown fat tissues were harvested and weighed; liver, spleen and kidney were harvested and weighed as well. Before sacrifice, glucose tolerance test was performed on all mice as described before.

Animal Study with Pure Trans-Stilbene Glycoside and Pure Cis-Stilbene Glycoside with Male CF-1 Mice Male CF-1 mice were selected as the model for type 2 diabetes. The mice were kept on Western HFD for 12 weeks and were divided into five groups with 10 each. Group I: Normal control which had free access to drinking water and normal Chow; Group II: Diabetic control which had free access to drinking water and Western HFD; Group III: Treatment group which had free access to drinking water with 0.01% of pure trans-stilbene glycoside and HFD;

Group IV: Treatment group which had free access to drinking water with 0.01% of pure cis-stilbene glycoside and Western HFD. Group V: Positive control group which had free access to drinking water with 0.01% of caffeine and Western HFD. Body weight, food and water uptake of the mice were taken on a regular basis. After 12 weeks, all the experimental mice were sacrificed. Body weight, blood glucose and blood insulin levels were evaluated as described before. Glucose tolerance test was also carried out at the end of the study.

PEPCK Assay with Pure Trans-Stilbene Glycoside and Pure Cis-Stilbene Glycoside Aside from animal study, both trans- and cis-stilbene glycoside will be evaluated for their effects on phosphoenolpyruvate carboxykinase (PEPCK), which is the key enzyme catalyzing the first step in hepatic gluconeogenesis. Glucagon and stress hormones, such as glucocorticoids, upregulate PEPCK gene expression in hepatocytes via a cyclic AMP (cAMP)-dependent pathway. Alternatively, insulin strongly represses PEPCK transcription through the activation of the phosphoinositide-3 kinase (PI3K) pathway 170. Normally, the increase in blood glucose levels after food intake stimulates the secretion of insulin from the pancreas. This increase in blood insulin concentration then leads to the down-regulation of PEPCK gene expression and, subsequently, the cessation of gluconeogenesis by the liver. Insulin resistant hepatocytes, however, are unable to effectively convey the insulin signal, leading to an increase in PEPCK mRNA transcription 171. Thus, the glucose synthesis persists despite a high blood glucose concentration. The compounds that are able to repress PEPCK expression and overcome insulin resistance could constitute a new class of glucose lowering agents 172.

The HepG2 cells were plated in 24-well tissue culture plates and were grown to near confluence in Dulbecco's modified Eagle's medium containing 2.5% (vol/vol) newborn calf serum and 2.5% (vol/vol) fetal calf serum. Cells were treated for 8 h with 500 nM dexamethasone and 0.1 mM 8-CTP-cAMP (Dex-cAMP) to induce PEPCK gene expression together with test compounds (5 µM trans-stilbene glycoside and 5 µM cis-stilbene glycoside).

Total RNA was extracted from HepG2 cells using Trizol reagent, following the manufacturer's instructions. RNA was quantified spectrophotometrically by absorbance measurements at 260 and 280 nm. Quality of RNA was assessed by separation in gel electrophoresis. RNA was then treated with Dnase1 (Invitrogen), following the manufacturer's guidelines, to remove any traces of DNA contamination. The cDNAs were synthesized with 2.5 g of RNA for each sample, using Stratascript reverse transcriptase (Stratagene, La Jolla, Calif.), following the manufacturer's protocol. The synthesized cDNAs were diluted fourfold. Five microliters of each of these diluted samples was used for PCR reactions of 25 ηL final volume. The other components of the PCR reactions were 0.5 ηL of 6 ηM gene-specific primers and 12.5 ηL of Brilliant SYBR Green PCR master mix (containing green jump-start Taq ready mix). ROX (Stratagene, La Jolla, Calif.) was used as a reference dye. The primers were selected using the Primer Express version 2.0 software (Applied Biosystems, Foster City, Calif.). These primers generated a 76-bp product from β-actin mRNA. The intron-spanning forward primer was selected to cover the exon 9-10 boundary. The reverse primer was selected from exon 10. The oligos were synthesized by IDT. These primers generated a 74-bp product from PEPCK mRNA and a 207-bp product from genomic DNA.

Quantitative PCR (qPCR) amplifications were performed on an MX3000p system (Stratagene, La Jolla, Calif.) using one cycle at 50° C. for 2 min and one cycle of 95° C. for 10 min, followed by 40 cycles of 15 s at 95° C. and 1 min at 60° C. The dissociation curve was completed with one cycle of 1 min at 95° C., 30 s at 55° C., and 30 s at 95° C. Non-RT control and no-template control were included in each experiment as quality control steps.

PEPCK mRNA expressions were analyzed using the ΔΔCT method and normalized with respect to the expression of the β-actin house keeping gene. The ΔΔCT Values obtained from these methods reflect the relative mRNA quantities for a specific gene in response to a treatment as relative to a calibrator. The Dex-cAMP treatment (positive control) served as the calibrator sample in this study. The PECPK gene expression of the calibrator sample was assigned to a value of 1.0. A value of <1.0 indicates transcriptional down-regulation (inhibition of gene expression) relative to the calibrator. Amplification of specific transcripts was further confirmed by obtaining melting curve profiles. All samples were run in duplicate.

Results

(1) NMR and MS for Trans- and Cis-Stilbene Glycoside

Figure 8:
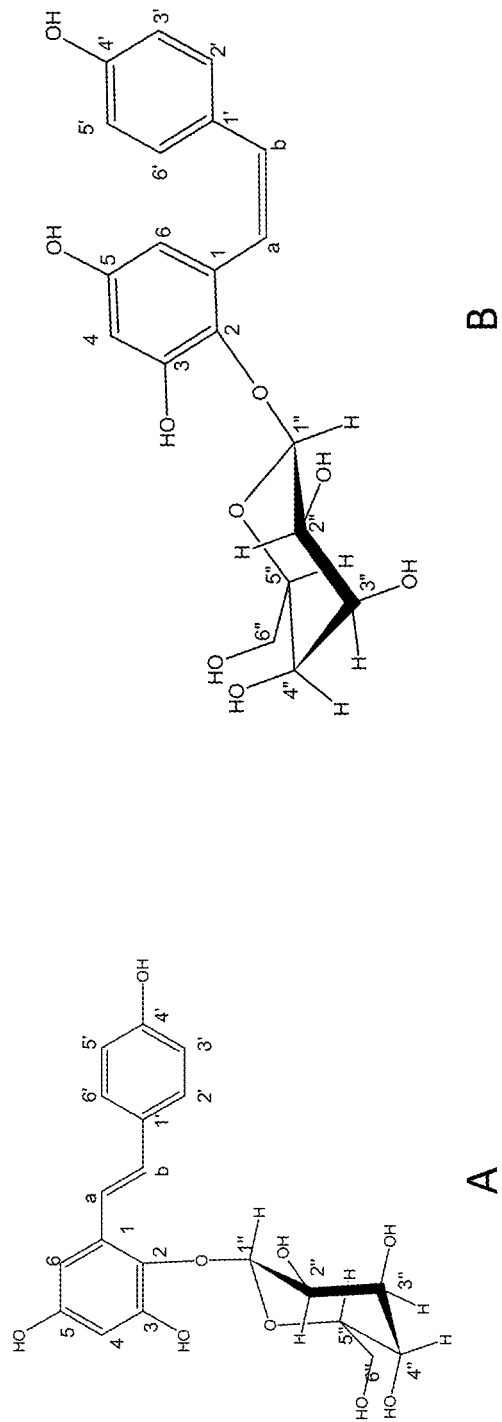
FIG. 8 illustrates chemical structures of (A) trans-stilbene glycoside and (B) cis-stilbene glycoside.
Figure 9:
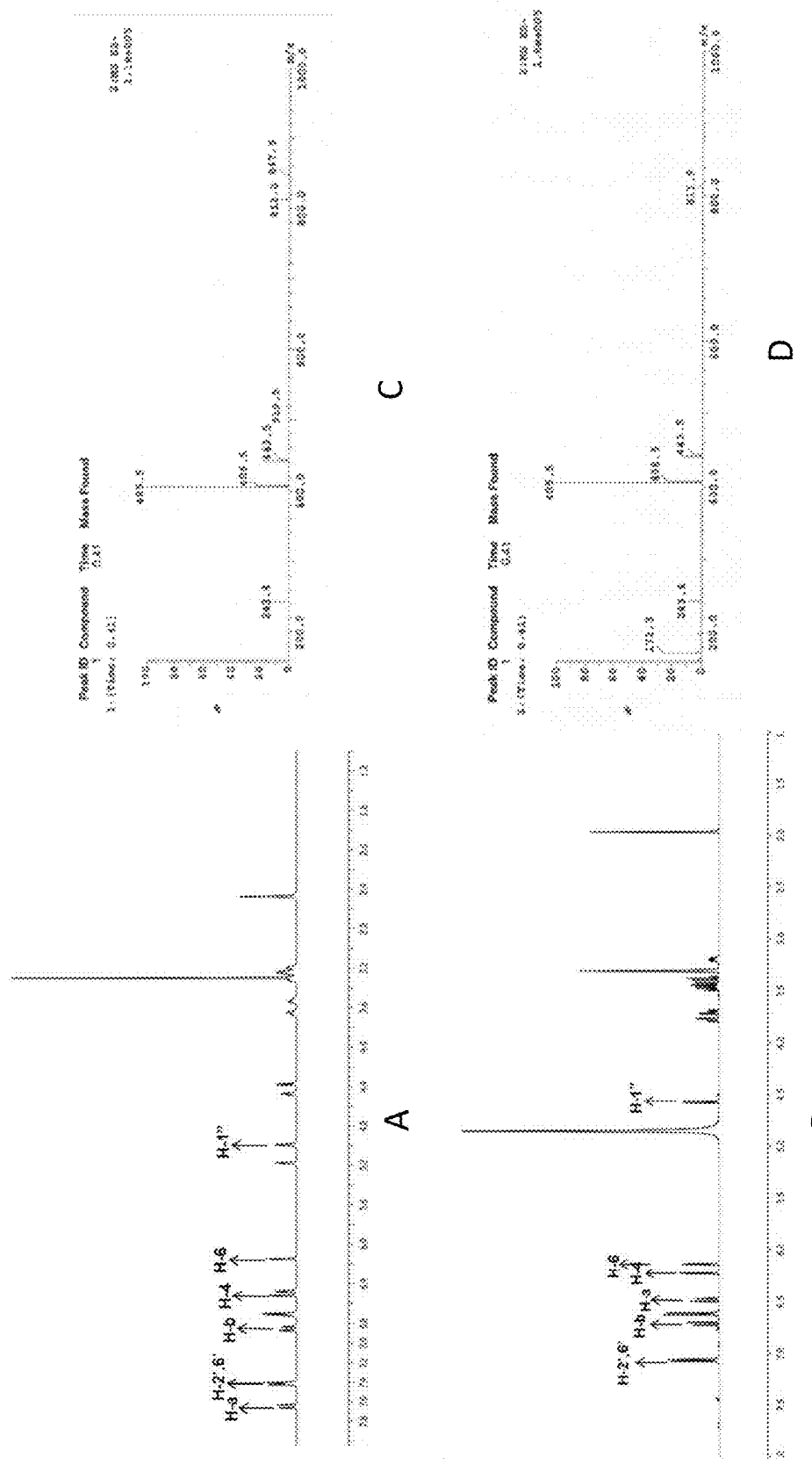
FIG. 9 shows NMR and LC-MS spectrums of trans-stilbene glycoside and cis-stilbene glycoside.

Trans-stilbene glycoside and cis-stilbene glycoside were identified with $^1$H and $^{13}$C NMR spectra as well as LC-MC spectrum by comparing to literature, structures shown in FIG. 8. For trans-stilbene glycoside, $^1$H-NMR (CD$_3$OD, 500 MHz) δ: 3.34-3.79 (6H, m, sugar H), 4.50 (1H, d, J=7.8 Hz, H-1"), 6.24 (1H, d, J=2.8 Hz, H-6), 6.61 (1H, d, J=2.8 Hz, H-4), 6.75 (2H, d, J=6.7 Hz, H-3',5'), 6.91 (1H, d, J=16.4 Hz, H-b), 7.44 (2H, dd, J=1.9, 6.7 Hz, H-2',6'), 7.70 (1H, d, J=16.4 Hz, H-a); $^{13}$C-NMR (CD$_3$OD, 500 MHz).

For cis-stilbene glycoside, $^1$H-NMR (CD$_3$OD, 500 MHz) δ: 3.39-3.82 (6H, m, sugar H), 4.58 (1H, d, J=7.6 Hz, H-1"), 6.15 (1H, d, J=2.8 Hz, H-6), 6.24 (1H, d, J=2.8 Hz, H-4), 6.50 (1H, d, J=12.2 Hz, H-a), 6.62 (2H, d, J=8.5 Hz, H-3',5'), 6.73 (1H, d, J=12.2 Hz, H-b), 7.08 (2H, d, J=8.5 Hz, H-2',6'); $^{13}$C-NMR (CD$_3$OD, 500 MHz).

The $^1$H-NMR spectrum of cis-stilbene glycoside was very similar to that of trans-stilbene glycoside, with the exception of the coupling constants of the vinylic protons signals (H-a and H-b), indicating the presence of two cis-coupled vinylic protons at δ6.71 (H-b) and 6.47 (H-a). The $^{13}$C-NMR spectrum of cis-stilbene glycoside exhibited two chemically equivalent aromatic carbons at $\delta_c$ 131.4 (C-2'/C-6') and $\delta_c$ 115.9 (C-3'/C-5').

The negative mass spectrum of trans-stilbene glycoside and cis-stilbene glycoside showed a [M-1]$^-$ ion at m/z 405. The fragment ion peak m/z 405 generated a main fragment ion [M-glc-1]$^-$ at m/z 243, which can be considered characteristic of the presence of an aglycone moiety.

Anti-Diabetic Effect of Extracts of Trans- and Cis-Stilbene Glycoside

Figure 10:
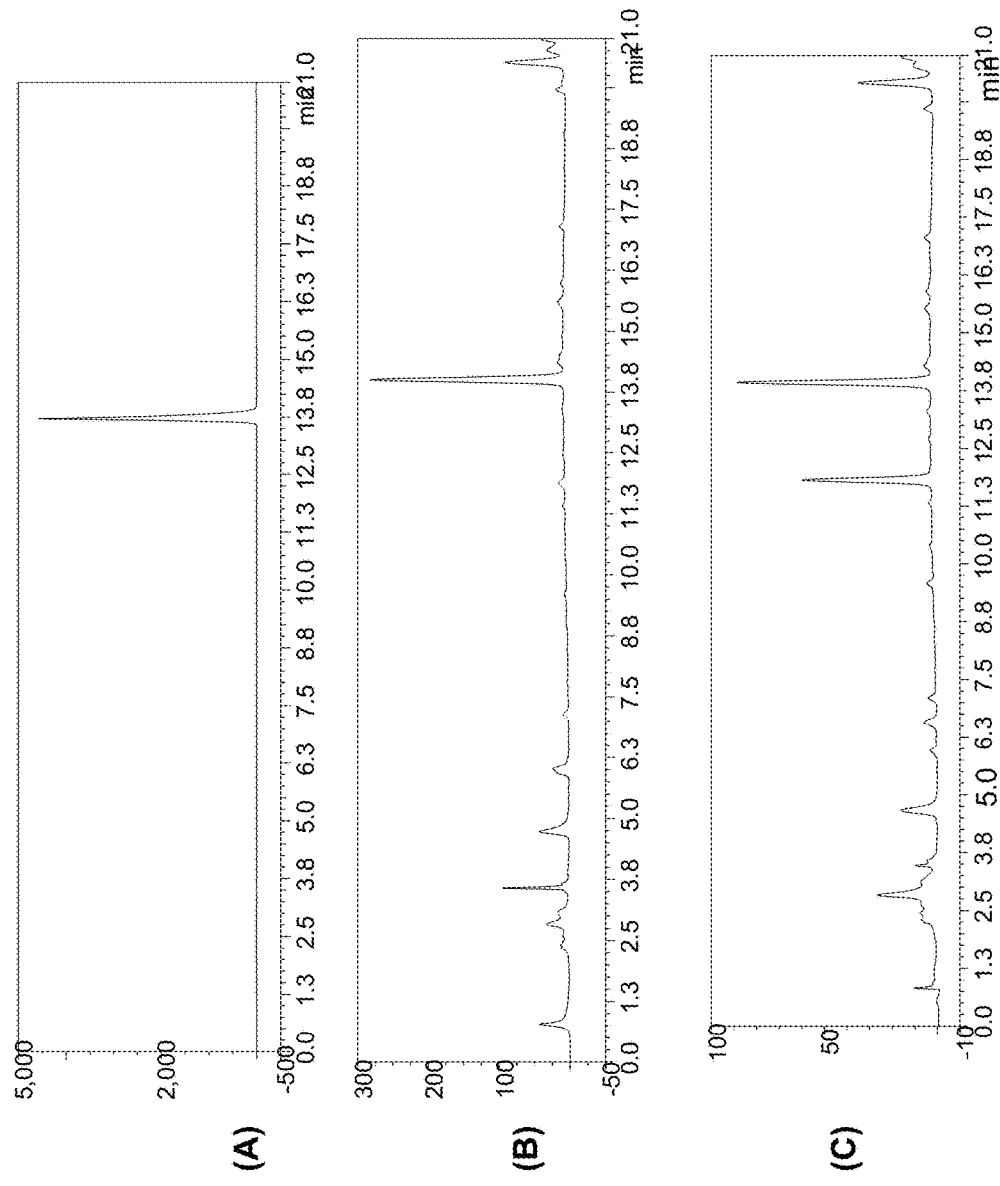
FIG. 10 includes HPLC chromatograms for the three solutions used in the animal study to investigate possible anti-diabetic effect of cis-stilbene glycoside.
Figure 11:
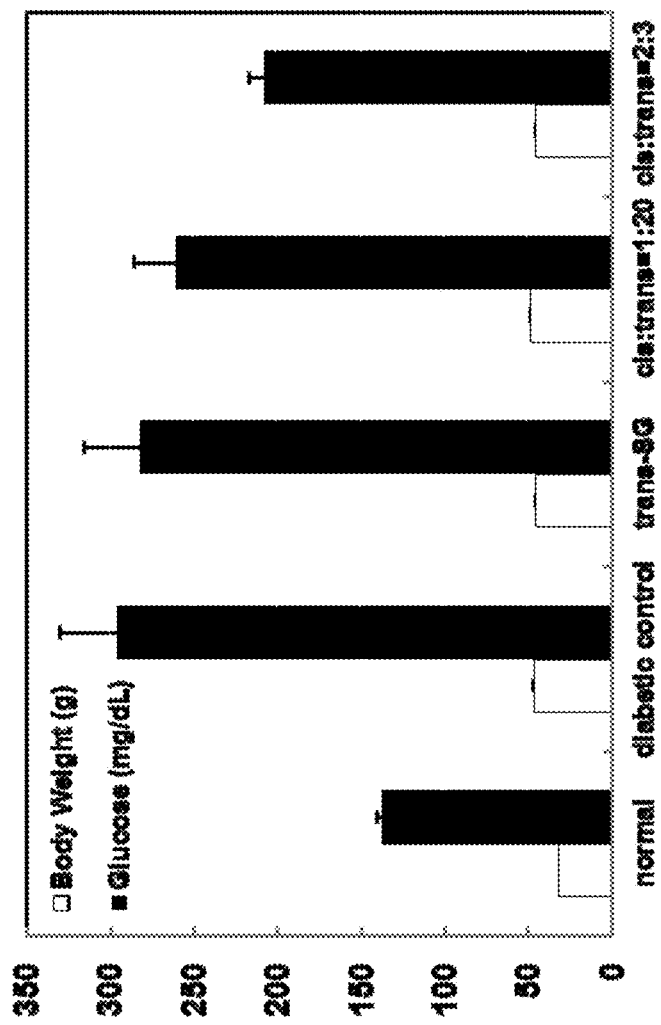
FIG. 11 is a bar diagram showing anti-diabetic effects of trans-stilbene glycoside and cis-stilbene glycoside in different proportions.

Female KK mice were fed with Western HFD for 18 weeks to induce a model for type 2 diabetes. Three solutions were employed in the study: pure trans-stilbene glycoside (0.05% in drinking water), PM extract with trans-stilbene glycoside/cis-stilbene glycoside 1:20 (0.075% in drinking water) and PM extract enriched with cis-stilbene glycoside (trans-stilbene glycoside/cis-stilbene glycoside 2:3, 0.075% in drinking water), HPLC chromatograms as shown in FIG. 10. Body weight and blood glucose levels were monitored. From the results, none of the three solutions significantly decreased high fat induced body weight gain compared to diabetic control. As for blood glucose, it showed a decreasing trend of blood glucose with increasing level of cis-stilbene glycoside in the extract. See FIG. 11. And the only solution which showed a significant hypoglycemic effect was the cis-stilbene glycoside enriched extract (p<0.05), while the other two did not. Considering the solution in group 3 was obtained from overnight exposure of solution in group 2 under UV-light and the only difference between the two extracts is the level of cis-stilbene glycoside, this data suggested possible anti-diabetic effect of cis-stilbene glycoside. However this effect needs to be confirmed by carrying out animal studies with pure trans- and cis-stilbene glycoside. In the present study HFD induced female KK mouse model was utilized to reduce cost of transgenic KK CgAy/j mice, however due to limited supply of KK mice and the length of time it takes for KK mice to develop obesity and hyperglycemia, it was necessary to explore other options for a suitable type 2 diabetes animal model which is economical, reliable and mimics human type 2 diabetes.

(3) Identifying a Model for Type 2 Diabetes

Two strains of mice were identified as possible candidates for diet induced diabetes model: C57BL/6J (C57) mice and CF-1 mice, and both male and female mice were evaluated. All mice were fed either a high-fat diet (58% energy by fat) or a normal diet (11% energy by fat), and body weight and blood glucose levels were taken at weeks 5, 8 and 12; glucose tolerance test also evaluated at the end of the study.

For C57 strain, both female and male mice had higher body weight at week 12 when fed a HFD compared to those on normal diet: F-HF group was 40.2% heavier than F-control while M-HF group was 11.8% heavier compared with M-control. Circulating blood glucose displayed a slight increasing trend from week 5 to week 8 except for M-HF, which decreased from 172.10 to 156.33 mg/dL; not much difference in blood glucose was shown from week 8 to week 12 except for M-control. For glucose tolerance test M-control group was missing because male C57 mice on normal diet displayed aggressive behaviors and by the end of study they were either injured or dead. Both male and female mice on HF diet displayed significant glucose intolerance since 30 minutes after glucose injection blood glucose rapidly rose to 266.78 and 256.50 mg/dL, respectively, nearly doubling the level before glucose injection. For lipid profile, not much difference was shown in all groups for the three parameters: triglycerides, HDL and LDL, except for triglycerides in M-HF group which was slightly higher than M-control, 64.67 versus 50 mg/dL. Body fat including parametrial fat and retro-peritoneal fat were much heavier in HF groups compared to control groups, and greater fat accumulation was observed in female mice. Weight of important organs, including pancreas, liver and kidney, were slightly higher in HF groups.

CF-1 mice became very obese at the end of 12 weeks, with the weight of M-HF mice being the highest of all, 53.4% heavier than F-control and 13.4% heavier than M-control. For nonfasting glucose, M-HF displayed a high level as early as week 5 and remained the highest throughout the course of 12 weeks, while F-HF had no significant difference in blood glucose from the control group. It was also M-HF group that displayed the highest degree of glucose intolerance: 30 minutes after glucose injection, blood glucose jumped to 358.2 mg/dL compared to an initial reading of 134.7 mg/dL, significantly higher than other three groups as well; after 120 minutes, it remained elevated at 192 mg/dL. The trend for lipid profile, fat mass and organ mass in CF-1 mice was similar to that of C57 mice. All information taken together, male CF-1 mice on HF diet was selected as the model for type 2 diabetes, as it is characterized with obesity, elevated blood sugar and a high level of glucose intolerance, which is very similar to human type 2 diabetes, and is absent for any aggressive behaviors.

(4) Anti-Diabetic Effect of Pure Trans- and Cis-Stilbene Glycoside

Figure 12:
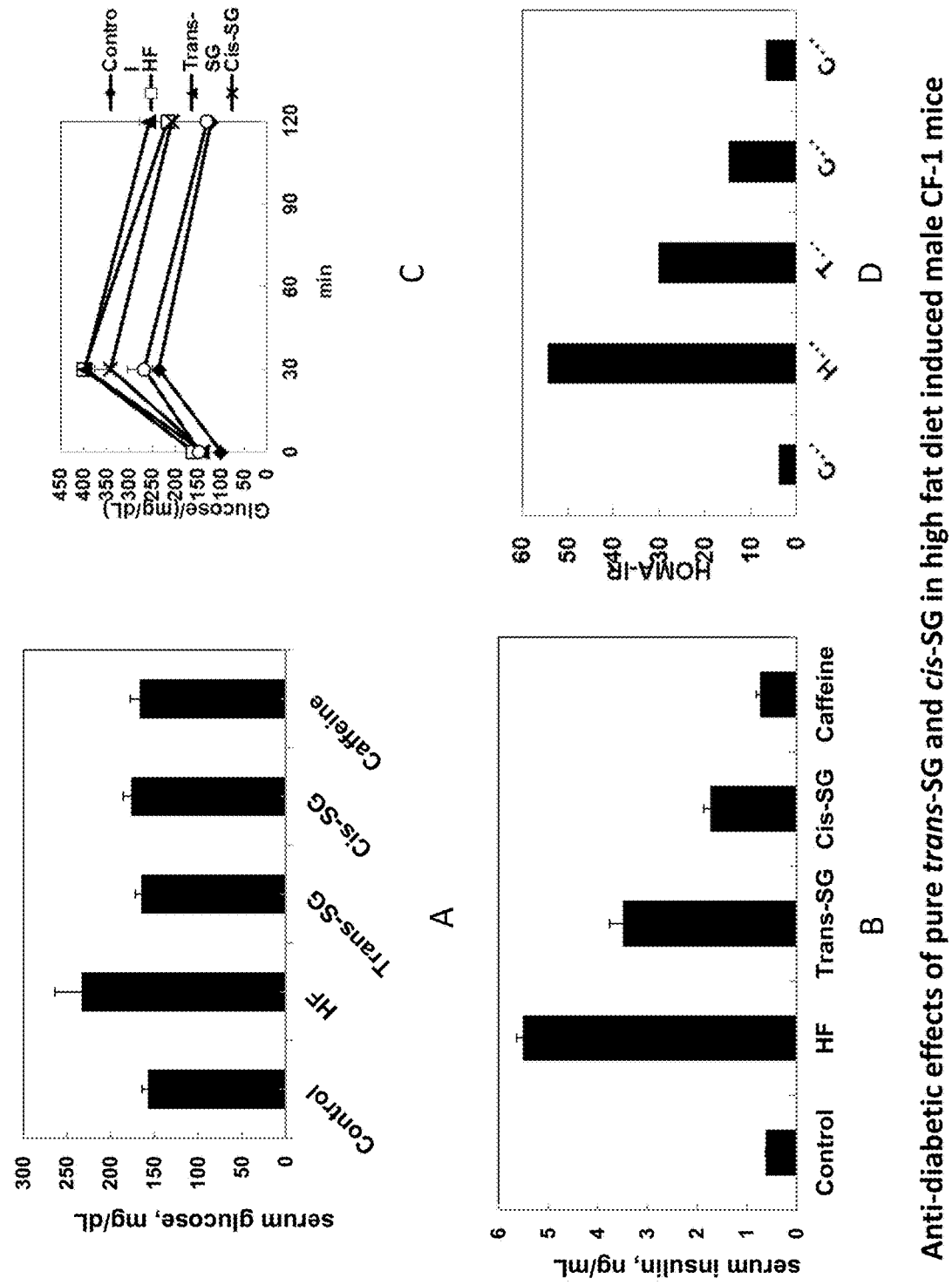
FIG. 12 is a diagram showing Anti-diabetic effects of pure trans-stilbene glycoside and cis-stilbene glycoside in high fat diet induced male CF-1 mice.

After identifying diet-induced male CF-1 mice as the model animal, and obtaining cis-stilbene glycoside from isomerization of trans-stilbene glycoside and purification with Prep-HPLC, the anti-diabetic effects of pure cis- and trans-stilbene glycoside was tested in the new model, and caffeine was used as a positive control. As evident in FIG. 12, both isomers of stilbene glycoside (0.01% in drinking water) could significantly decrease the serum glucose level in the male CF-1 mice after HFD treatment for 12 weeks, similar to that of caffeine. In GTT, HF group showed glucose intolerance test since blood glucose increased sharply 30 min after the intraperitoneal injection of glucose solution and remained at a very high level after 120 min. In contrast, the rise in blood glucose level was greatly suppressed by cis-stilbene glycoside; however, the effect on glucose intolerance was absent in trans-stilbene glycoside treated group. HF mice had a much higher level of serum insulin than normal control at the end of the study and in both stilbene glycoside treatment groups insulin levels were significantly lowered. After calculating the HOMA-IR with the equation HOMA-IR=Glucose*Insulin/405 [159], insulin resistance was found to be greatly elevated in HF group but reduced in all experimental groups. Calculated HOMA-IR in cis-stilbene glycoside group was 102.7% lower than that in trans-stilbene glycoside group, indicating cis-stilbene glycoside had a much stronger effect in alleviating insulin resistance than trans-stilbene glycoside.

(5) PEPCK Assay

Figure 13:
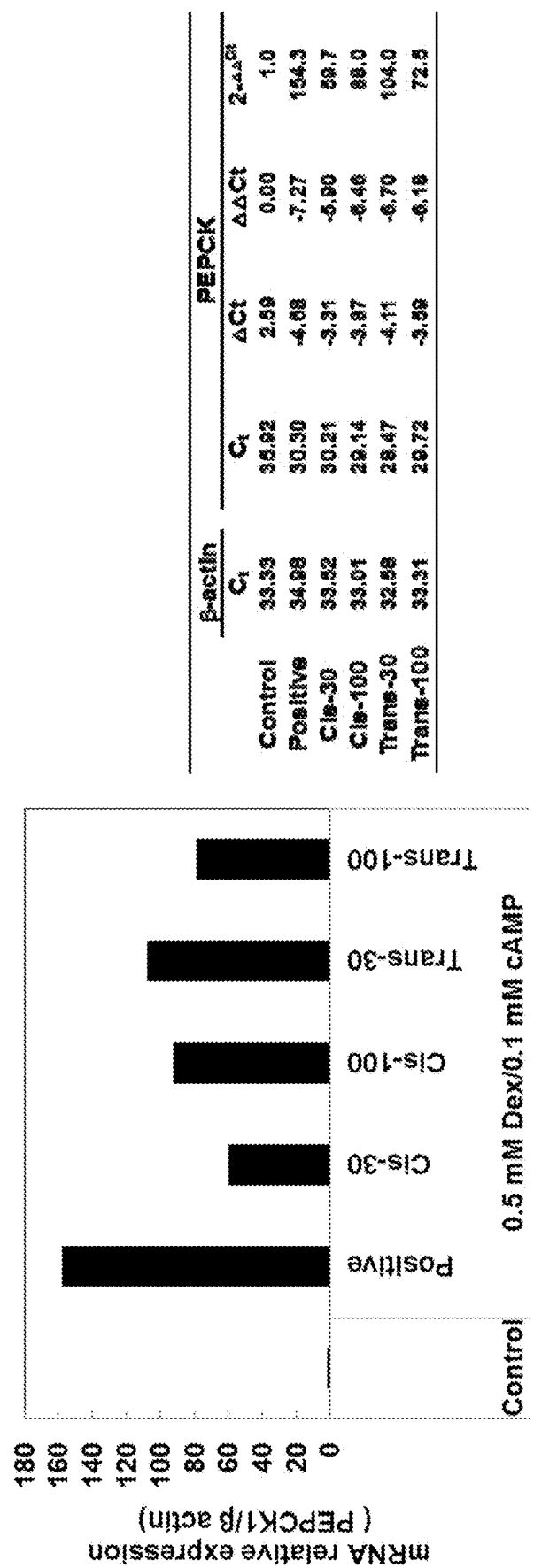
FIG. 13 is a diagram showing PEPCK mRNA expression normalized to β-actin.

Real-time PCR, also called quantitative PCR or qPCR, can provide a simple and elegant method for determining the amount of a target sequence or gene that is present. PEPCK assay was performed with liver HepG2 cells and the level of PEPCK mRNA from real-time PCR is normalized with β-actin. Dex/cAMP could induce the transcription of PEPCK gene and as seen in FIG. 13A, both cis-stilbene glycoside and trans-stilbene glycoside could effectively suppress the up-regulation. However no dose-dependent pattern was observed, as cis-stilbene glycoside suppressed more efficiently at 30 μM than at 100 μM, while for trans-stilbene glycoside higher concentration resulted in lower level of PEPCK transcription. This agrees with the results from the comparative Ct method, where cis-stilbene glycoside (30 μM) had a 61.7% reduction compared to Dex/cAMP group while trans-stilbene glycoside (100 μM) had 53.3% reduction. Therefore cis-stilbene glycoside was found to be more effective than trans-stilbene glycoside in ameliorating Dex/cAMP-induced PEPCK transcription in HepG2 cells.

Example 4. The Extraction of 2,3,5,4'-Tetrahydroxystilbene 2-O-β-Glucopyranoside Stilbene Glycoside from Foti (*Polygonum Multiflorum* or Heshouwu)

Extraction: The root of *Polygonum multiflorum* (PM) was purchased from a commercial medicinal store located in Huanggang city, Hubei province of China. There are two types of root available: raw foti root and processed foti root. Raw root has a pale white color and is directly from the sundry after washing and cleaning. The processed foti is processed from the raw root: i.e. the raw root was washed and cleaned first then repeated steam and sundry (at least 4 steam/sundry cycles). Both types of foti are commercially available. The purchased foti root samples were dried in an oven at 50° C. for 12 hour, then ground to fine powder. The resulted powder was stored in a dry and dark container. 10 g of foti root powder was weighed and placed in a brown round bottom flask. To the flask, 100 ml of 60% aqueous ethanol was added for the extraction (solid:liquid ratio=1:10). The extraction was conducted at ambient temperature for specified time on Table 2 (1-5 days). Upon the finish of the extraction, the mixture was filtered in vacuo and the solid waste was washed with 40 ml of 60% aqueous ethanol. The filtrate was combined and concentrated in vacuo to yield a solid sample.

was filtered and residue was washed. The filtrate was combined and concentrated, dried and weight. Analytical samples were collected for each extraction sample. The results, i.e. content of both trans-stilbene glycoside and cis-stilbene glycoside in each raw foti sample, conversion rate from trans-stilbene glycoside to cis-stilbene glycoside, were summarized in Table 2.

Conclusion: for raw foti, the optimum immersement time is 4 days, to have a maximum extraction rate of stilbene glycoside, at the highest extraction rate of 4.5% of total stilbene glycoside.

Example 6. The Extraction Rate at Different Time for Processed Foti

As illustrated in Table 2, both processed foti were immersed in water. The ratio of solid to solvent (water) was 1:10. Samples were collected at different days from day 1, day 2, days 3, day 4 to day 5. When the extraction process

TABLE 2

The influence of different varieties and different soaking time on the extraction yield

| Types and time | stilbene glycoside | Area on HPLC | Total area | Concentration (mg/mL) | Weight of residue (g) | Extraction rate (%) |
|---|---|---|---|---|---|---|
| Raw foti (1 day) | cis-stilbene glycoside | 11072 | 194994 | 0.0099 | 2.63 | 2.60 |
| | trans-stilbene glycoside | 183922 | | | | |
| Raw foti (2 day) | cis-stilbene glycoside | 12250 | 193322 | 0.0098 | 3.08 | 3.03 |
| | trans-stilbene glycoside | 181072 | | | | |
| Raw foti (3 day) | cis-stilbene glycoside | 13367 | 253501 | 0.0117 | 2.72 | 3.17 |
| | trans-stilbene glycoside | 240134 | | | | |
| Raw foti (4 day) | cis-stilbene glycoside | 15695 | 358117 | 0.0148 | 3.06 | 4.54 |
| | trans-stilbene glycoside | 342422 | | | | |
| Raw foti (5 day) | cis-stilbene glycoside | 3171 | 275593 | 0.0123 | 2.95 | 3.63 |
| | trans-stilbene glycoside | 272422 | | | | |
| Processed foti (1 day) | cis-stilbene glycoside | 14878 | 219642 | 0.0106 | 2.37 | 2.52 |
| | trans-stilbene glycoside | 204764 | | | | |
| Processed foti (2 day) | cis-stilbene glycoside | 16516 | 491953 | 0.0189 | 2.8 | 5.29 |
| | trans-stilbene glycoside | 475437 | | | | |
| Processed foti (3 day) | cis-stilbene glycoside | 38358 | 147573 | 0.0084 | 2.76 | 2.33 |
| | trans-stilbene glycoside | 109215 | | | | |
| Processed foti (4 day) | cis-stilbene glycoside | 13015 | 186877 | 0.0096 | 2.52 | 2.43 |
| | trans-stilbene glycoside | 173662 | | | | |
| Processed foti (5 day) | cis-stilbene glycoside | 16520 | 225983 | 0.0108 | 2.78 | 3.01 |
| | trans-stilbene glycoside | 209463 | | | | |

Example 5. The Extraction Rate at Different Time for Raw Foti

As illustrated in Table 2, raw foti was immersed in water. The ratio of solid to solvent (water) was 1:10. Samples were collected at different days, at day 1, day 2, days 3, day 4 and day 5. When the extraction process was stopped, the mixture was stopped, the mixture was filtered and residue was washed. The filtrate was combined and concentrated, dried and weight. Analytical samples were collected for each extraction sample. The results, i.e. content of both trans-stilbene glycoside and cis-stilbene glycoside in each processed sample, conversion rate from trans-stilbene glycoside to cis-stilbene glycoside, were summarized in Table 2.

Conclusion: for processed foti, the optimum immersement time is 2 days, to have a maximum extraction rate of stilbene glycoside, at the highest extraction rate of 5.29% of total stilbene glycoside.

Example 7. Purification and Isolation of Stilbene Glycoside From (the Above) Extracted Solid Residue One g of dried solid residue obtained above (Example 4) was suspended in 10 ml of water solution. The solution was applied to an HP-20 (microporous resin) packed liquid chromatography. The following are detailed experimental procedure.

Microporous resin HP-20 was activated prior to use according to manufacture's instruction. The obtained dried extract (solid residue from Example 4) was then subjected to column chromatography packed with macroporous resin (HP-20). The column was eluted with a series of mixed solvents of ethanl and water. The ethanol content is from 0% to 60% in water. Therefore, the eluting process was eluted with water, 10% ethanol, 20%, 30%, 40%, and 50% followed by 60% aqueous ethanol. Fractions of eluted solution were collected to different flask containers. Each fraction was analyzed with an HPLC analysis and the ones with pure trans-stilbene glycoside were combined and concentrated in vacuo and then lyophilized. The purity of trans-stilbene glycoside thus isolated from the liquid chromatography with macroporous resin stationary phase and aqueous ethanol mobile phase was over 99% as determined by HPLC and $^1$H NMR.)

Example 8. Effect of Different Concentrations of Ethanol Solution on the Elution of Stilbene Glycoside The collected samples from above (Example 4) were analyzed with an HPLC that has established standard curves of both trans-stilbene glycoside and cis-stilbene glycoside using pure trans-stilbene glycoside and cis-stilbene glycoside. The analysis results obtained from HPLC measurement for different solvents used in eluting trans-stilbene glycoside showed that only three solvent mixture contained trans-stilbene glycoside: 30%, 40% and 50%. The fraction from 40% aqueous ethanol has the maximum content of trans-stilbene glycoside with a purity of above 98%.

Conclusion: 40% aqueous ethanol is the optimum solvent to elute trans-stilbene glycoside from the mixture of extracted solid from the powder of foti.

Example 9. The Influence of Time on the Transformation from Trans-Stilbene Glycoside to Cis-Stilbene Glycoside Under 365 nm UV Wavelength Forty mg of trans-stilbene glycoside was dissolved in 2 mL of dd water (double distilled water) under UV-light (365 nm). The reaction was monitored with HPLC (high performance liquid chromatography) analysis. Analytical samples were collected at 1 h, 2 h, 3 h, 4 h, 5 h, 6 h, 7 h and 15 h, respectively. The collected samples were analyzed by HPLC with standard curves to quantify both trans-stilbene glycoside and cis-stilbene glycoside accurately. The transformation rate from trans-stilbene glycoside to cis-stilbene glycoside was calculated based on the standard curve on the HPLC. The results were shown in Table 3.

Conclusion: Under 365 nm UV irradiation, the maximum conversion rate is 95% and the time reached the highest conversion rate is at 7 h. At 5 h, the conversion rate is reached 94%.

TABLE 3

Relationship between conversion and irradiation time under 365 nm UV light exposure

| Time under 365 nm UV | stilbene glycoside | Area from HPLC | Ratio of cis-stilbene glycoside to trans-stilbene glycoside | Total area | Rate of conversion |
|---|---|---|---|---|---|
| 0 h | cis-stilbene glycoside | 5288 | 1:99 | 528821 | 0% |
|  | trans-stilbene glycoside | 523533 |  |  |  |
| 1 h | cis-stilbene glycoside | 464255 | 88:12 | 527563 | 88% |
|  | trans-stilbene glycoside | 63308 |  |  |  |
| 2 h | cis-stilbene glycoside | 470384 | 89:11 | 528521 | 89% |
|  | trans-stilbene glycoside | 58137 |  |  |  |
| 3 h | cis-stilbene glycoside | 474926 | 90:10 | 527695 | 90% |
|  | trans-stilbene glycoside | 52769 |  |  |  |
| 4 h | cis-stilbene glycoside | 477356 | 91:9 | 524567 | 91% |
|  | trans-stilbene glycoside | 47211 |  |  |  |
| 5 h | cis-stilbene glycoside | 495340 | 94:6 | 526957 | 94% |
|  | trans-stilbene glycoside | 31617 |  |  |  |
| 6 h | cis-stilbene glycoside | 495001 | 94:6 | 526597 | 94% |
|  | trans-stilbene glycoside | 31596 |  |  |  |
| 7 h | cis-stilbene glycoside | 500165 | 95:5 | 526489 | 95% |
|  | trans-stilbene glycoside | 26324 |  |  |  |
| 15 h | cis-stilbene glycoside | 497512 | 95:5 | 523697 | 95% |
|  | trans-stilbene glycoside | 26185 |  |  |  |

Example 10. The Influence of Time on the Transformation from Trans-Stilbene Glycoside to Cis-Stilbene Glycoside Under 254 nm UV Wavelength Forty mg of trans-stilbene glycoside was dissolved in 2 mL of dd water (double distilled water) under UV-light (254 nm). The reaction was monitored with HPLC analysis. Analytical samples were collected at 1 h, 2 h, 3 h, 4 h, 5 h, 6 h, 7 h and 15 h, respectively. The collected samples were analyzed by HPLC with standard curves to quantify both trans-stilbene glycoside and cis-stilbene glycoside accurately. The transformation rate from trans-stilbene glycoside to cis-stilbene glycoside was calculated based on the standard curve on the HPLC. The results were shown in Table 4.

Conclusion: Under 254 nm UV irradiation, the maximum conversion rate is 95% and the time reached the highest conversion rate is at 15 h. At 5 h, the conversion rate is reached 88%.

TABLE 4

Relationship between conversion and irradiation time under 254 nm UV light exposure

| Time under 254 nm UV | stilbene glycoside | Area from HPLC | Ratio of cis-stilbene glycoside to trans-stilbene glycoside | Total area | Rate of conversion |
|---|---|---|---|---|---|
| 0 h | cis-stilbene glycoside | 5288 | 1:99 | 528821 | 0 |
|  | trans-stilbene glycoside | 523533 |  |  |  |
| 1 h | cis-stilbene glycoside | 290654 | 55:45 | 528461 | 55% |
|  | trans-stilbene glycoside | 237807 |  |  |  |
| 2 h | cis-stilbene glycoside | 393488 | 75:25 | 524651 | 75% |
|  | trans-stilbene glycoside | 131163 |  |  |  |
| 3 h | cis-stilbene glycoside | 419650 | 80:20 | 524563 | 80% |
|  | trans-stilbene glycoside | 104913 |  |  |  |
| 4 h | cis-stilbene glycoside | 447307 | 85:15 | 526243 | 85% |
|  | trans-stilbene glycoside | 78936 |  |  |  |
| 5 h | cis-stilbene glycoside | 464518 | 88:12 | 527861 | 88% |
|  | trans-stilbene glycoside | 63343 |  |  |  |
| 6 h | cis-stilbene glycoside | 471187 | 90:10 | 523541 | 90% |
|  | trans-stilbene glycoside | 52354 |  |  |  |
| 7 h | cis-stilbene glycoside | 491106 | 94:6 | 522453 | 94% |
|  | trans-stilbene glycoside | 31347 |  |  |  |
| 15 h | cis-stilbene glycoside | 495200 | 95:5 | 521263 | 95% |
|  | trans-stilbene glycoside | 26063 |  |  |  |

Example 11. The Influence of UV Wavelength on the Transformation from Trans-Stilbene Glycoside to Cis-Stilbene Glycoside By comparing Table 3 and Table 4, the two sets of data, it can be concluded that the conversion rate of the stilbene glycoside (from trans-stilbene glycoside to cis-stilbene glycoside) solution irradiated with 365 nm ultraviolet light is always higher than that of the stilbene glycoside irradiated by ultraviolet light at 254 nm. Moreover, the time needed for the cis-trans isomerization to reach a balance is an imported factor for the conversion. The time is much shorter to reach the isomerization balance at the irradiation of 365 nm UV wavelength, indicating that at 365 nm UV irradiation, the conversion is faster and more effective. For instance, the standard trans-stilbene glycoside solution irradiated with 365 nm ultraviolet light takes about 7 hours to achieve the optimal conversion, whereas, the standard solution irradiated with 254 nm ultraviolet light takes about 15 hours to reach the optimal conversion.

Conclusion: in terms of conversion rate and effectiveness from trans-stilbene glycoside to cis-stilbene glycoside, 365 nm is the optimal UV wavelength. At 5 hours, it reached the conversion of 94% of cis-stilbene glycoside from 1% or less of cis-stilbene glycoside at the beginning, whereas, at 254 nm at 5 hours, the maximum conversion is 88% of cis-stilbene glycoside.

Example 12. Purification of Cis-Stilbene Glycoside with Preparative High Performance Chromatography Pure trans-stilbene glycoside (0.2 g) was dissolved in water (20 ml) and placed under UV-light (365 nm) for 5 hours. The reaction was monitored with HPLC analysis. The solution after UV exposure was concentrated, filtered, and subjected to purification of cis-stilbene glycoside with a semi-preparative HPLC (Gilson Inc., Madison, Wis.) equipped with a Hypersil-C18 column (20×300 mm, 10 μm, Fisher) and mobile phase of acetonitrile and water. Pure fractions of cis-stilbene glycoside generated was piled, concentrated in vacuo and lyophilized to yield 0.12 g of. cis-stilbene glycoside as a pale white solid. The purity cis-stilbene glycoside thus prepared was over 99% as determined by HPLC and $^1$H NMR.

Example 13. Purification of Cis-Stilbene Glycoside with Recrystalization Method

Pure trans-stilbene glycoside (2 g) was dissolved in water (50 ml) and placed under UV-light (365 nm) for 5 hours. The reaction was monitored with HPLC analysis. The solution after UV exposure was concentrated, filtered, and subjected to recrystalization as detailed in the following. The solid residue after concentration was re-dissolved in water. The resulted solution was heated to close to the boiling point of water. Then ethanol was added to the heated solution with much care. When white precipitates were formed and the solution turned to cloudy, small amount of ethanol was added while heating. Addition of ethanol was continued till the solution turned to clear. The solution was cooled naturally to ambient temperature and then was placed to a refrigerator. The precipitate of the cis-stilbene glycoside was collected. The above recrytalization procedure was repeated. The collected cis-stilbene glycoside product was dried in a heated oven (40 oC) for 18 hours to yield 1.5 g of. cis-stilbene glycoside as a pale solid. The purity cis-stilbene glycoside thus prepared was over 99% as determined by HPLC and $^1$H NMR.

Conclusion: Recrystalization method was used for the first time in purifying cis-stilbene glycoside. Other recrystalization solvent system other than ethanol-water (Example 9) can be methanol/water; isopropyl/water; acetonitrile/water etc.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of processing *Polygonum multiflorum* (PM), the method comprising:
    crushing dried roots of PM to powder;
    extracting the PM powder with an ethanol solution under the room temperature for at least 2 days to obtain an ethanolic extract, the ratio of solution to solid being about 1:10 (v/w);
    evaporating and concentrating the ethanolic extract under reduced pressure to obtain a dried extract; and
    subjecting the dried extract to macroporous resin chromatography, followed by eluting the resin with ethanol solutions of different concentrations to obtain a first eluant;
    evaporating and drying the first eluant under reduced pressure to obtain PM extract powder;
    dissolving the obtained PM extract powder in an aqueous solution to obtain a PM solution; and
    placing the PM solution under UV light for 1 to 24 hours, whereby an UV-treated PM solution is obtained.

2. The method of claim 1, wherein the PM solution comprises trans-2,3,5,4-tetrahydroxystilbene 2-O-β-glucopyranoside (stilbene glycoside) at a concentration of 1-50 mg/ml.

3. The method of claim 1, wherein the PM solution contains trans-2,3,5,4-tetrahydroxystilbene 2-O-β-glucopyranoside (stilbene glycoside) at a concentration of 2-20 mg/ml.

4. The method of claim 2, wherein the UV light has a wavelength of approximately 365 nm.

5. The method of claim 4, wherein the PM solution is placed under the UV light for 5-15 hrs.

6. The method of claim 1, wherein the UV-treated PM solution comprises cis-stilbene glycoside and trans-stilbene glycoside, the ratio of cis-stilbene glycoside to trans-stilbene glycoside being greater than 1:1.

7. The method of claim 6, wherein the ratio of cis-stilbene glycoside to trans-stilbene glycoside is between 3:1 to 5:1.

8. The method of claim 6, wherein the ratio of cis-stilbene glycoside to trans-stilbene glycoside is at or greater than 10:1.

* * * * *